United States Patent
Moissl et al.

(10) Patent No.: US 11,701,022 B2
(45) Date of Patent: Jul. 18, 2023

(54) METHOD FOR CALIBRATING A BIOIMPEDANCE MEASURING DEVICE, AND MEDICAL DEVICES

(71) Applicant: Fresenius Medical Care Deutschland GmbH, Bad Homburg (DE)

(72) Inventors: Ulrich Moissl, Karben (DE); Paul Chamney, Tring (GB); Tobias Groeber, Heusenstamm (DE); Peter Wabel, Hosbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 39 days.

(21) Appl. No.: 16/734,921

(22) Filed: Jan. 6, 2020

(65) Prior Publication Data
US 2021/0204829 A1 Jul. 8, 2021

(51) Int. Cl.
*A61B 5/053* (2021.01)

(52) U.S. Cl.
CPC ...... *A61B 5/053* (2013.01); *A61B 2560/0228* (2013.01); *A61B 2560/0252* (2013.01)

(58) Field of Classification Search
CPC ............ A61B 5/053; A61B 2560/0228; A61B 2560/0252
See application file for complete search history.

(56) References Cited

U.S. PATENT DOCUMENTS

| | | | |
|---|---|---|---|
| 4,291,708 A | 9/1981 | Frei et al. | |
| 4,539,640 A | 9/1985 | Fry et al. | |
| 5,063,937 A | 11/1991 | Ezenwa et al. | |
| 2009/0043222 A1* | 2/2009 | Chetham | A61B 5/4878 600/547 |
| 2011/0054343 A1* | 3/2011 | Chetham | A61B 5/744 600/547 |
| 2021/0077717 A1* | 3/2021 | Srinivasan | G16H 40/63 |

FOREIGN PATENT DOCUMENTS

CN 1849092 A 10/2006

OTHER PUBLICATIONS

Birjukov et al., "Digitally controlled Reference Impendance Device for Test and Calibration of the Bio-Impendance Measurement System (BIMS) in a Network Environment," 13th International Conference on Electrical Bioimpedance and the 8th Conference on Electrical Impedance Tomography, IFMBE Proceedings, 2007, 276-279.

Li et al., "Reconfigurabie Bioimpendance Emulation System for Electrical Impendance Tomography System Validation," IEEE Transactions on Biomedical Circuits and Systems, Aug. 2013, 7(4):460-468.

PCT International Search Report and Written Opinion in International Appln. No. PCT/EP2020/088070, dated Mar. 29, 2021, 16 pages.

\* cited by examiner

*Primary Examiner* — Patrick Fernandes
*Assistant Examiner* — Joseph A Tombers
(74) *Attorney, Agent, or Firm* — Fish & Richardson P.C.

(57) ABSTRACT

The disclosure relates to new methods for calibrating or adjusting a bioimpedance measuring device. Furthermore, the present disclosure relates to a medical set or system, a medical measuring standard, a method for testing a bioimpedance measuring device, and a bioimpedance measuring device.

23 Claims, 10 Drawing Sheets

METHOD FOR CALIBRATING A BIOIMPEDANCE MEASURING DEVICE, AND MEDICAL DEVICES

BACKGROUND OF THE INVENTION

The measuring principle of bioimpedance measurements is well established. For measuring the impedance values, a current is applied to the patient via signal electrodes of a bioimpedance measuring device at a first site, and at another site, an impedance, present exists between the first site and the second site is measured using measuring electrodes of said device. The size or value of the impedance is determined over a frequency range applied via the measuring electrodes. Thus, measured values may result in an impedance curve from which a variety of parameters can be derived (overhydration, lean tissue, fat tissue, and the like). Bioimpedance measuring devices are described, e.g., in U.S. Pat. Nos. 5,063,937, 4,291,708 and 4,539,640.

The electronic implementation of the measuring principle makes it necessary to calibrate or adjust the bioimpedance measuring device because electronic components as well as the manufacture of the device are subject to a production-related mismatch or deficiency that is to be compensated by a calibration process on the finished device. Without this calibration, it is not certain that the measured impedance curve meets certain accuracy requirements. Since patient-specific parameters are determined from this impedance curve, or from individual values of this curve, the accuracy is a safety or health aspect. In particular, an error in the determination of overhydration is a circumstance directly affecting the health of the patient, because based on the determined overhydration the therapy is derived, which would then rely on incorrect or inaccurate information and thus could lead to a wrong, even life-threatening treatment in extreme cases.

SUMMARY OF THE INVENTION

The present disclosure describes methods for calibrating or adjusting a bioimpedance measuring device. Furthermore, the present disclosure describes a medical set (short also: set) or system, a medical measuring standard (short also: measuring standard), a method for testing a bioimpedance measuring device, and a bioimpedance measuring device.

In all of the aforementioned and following statements, the use of the expression "may be" or "may have" and so on, is to be understood synonymously with "preferably is" or "preferably has", and so on, respectively, and is intended to illustrate an embodiment according to the present disclosure.

Whenever numerical words are mentioned herein, the person skilled in the art shall understand them as indications of numerical lower limits. Hence, unless this leads to a contradiction evident to the person skilled in the art, the person skilled in the art shall comprehend for example "one" as encompassing "at least one". This understanding is also equally encompassed by the present disclosure as the interpretation that a numerical word, for example, "one" may alternatively mean "exactly one", wherever this is technically possible in the view of the person skilled in the art. Both meanings are encompassed by the present disclosure and apply herein to all used numerical words.

Whenever the terms "programmed" or "configured" are mentioned herein, these terms are used interchangeably.

Whenever the "disclosure" is referred to, the present invention is meant.

Whenever it is referred to an "embodiment," an embodiment according to the present invention is meant.

The information "top" and "bottom" are to be understood as spatial information referring to the situation or orientation of the respective element during intended use.

Hence, this disclosure describes methods for (at least partially) calibrating a bioimpedance measuring device. In some embodiments, the method encompasses the steps:

providing a bioimpedance measuring device;

providing a measuring standard (or: calibration standard) with a plurality of components (called, e. g., X, Y, Z), which may each be set or adjusted automatically and/or by a user in terms of their component characteristic or their component value (called, e.g., $x_1, x_2, \ldots x_m$ with regard to component X; $y_1, y_2, \ldots y_n$ with regard to component Y; $z_1, z_2, \ldots z_o$ with regard to component Z, with m, n and o being integers or natural numbers), so that a number ($|K|=m*n*o$) of combinations K of component values ($x_1, x_2, \ldots x_m; y_1, y_2, \ldots y_n; z_1, z_2, \ldots z_o$) may be set or adjusted at the measuring standard automatically and/or by the user;

providing a Calibration Database or Pool (CDB), wherein the Calibration Database or Pool (CDB) comprises $|CDB|$ combinations or sets of components values, wherein $|CDB|$ is smaller than $|K|$ (or $|CDB|<|K|$); and calibrating the bioimpedance measuring device by using the measuring standard and setting one of: some, each, all, maximally all of the $|CDB|$ combinations of component values from the Calibration Database or Pool (CDB) at the measuring standard, but not by setting or adjusting more than the $|CDB|$ combinations (i.e., by not using more than $|CDB|$ combinations; further parameters which are not combinations of component values, may be taken into account).

As is common in the mathematical notation $|CDB|$ stands for the number of elements comprised by the database or the pool called CDB which is understood as a set of entries, combinations, objects, elements, or the like. The same use of "| . . . |" is used throughout this application.

It is noted that the Calibration Database or Pool (CDB) as referred to herein may be a database as known, e. g., from computer science, e. g., an organized collection of data, generally stored in a storage device and accessible electronically from or by a computer system. However, the Calibration Database or Pool (CDB) may also be a collection of sets of entries, combinations and the like that are kept or stored in another or in a non-organized manner. The alternative term "pool" as used herein shall reflect this.

Irrespective whether the Calibration Database or Pool (CDB) is embodied as a database or as a less organized or unstructured entity like a pool, its entries or sets comprised do not necessarily be kept, stored or provided in or from a single place. Rather, its content may also be kept in several places such as different storage devices, folders, files, and the like.

In some embodiments, the medical set according to the present disclosure encompasses a measuring standard with a plurality of components (X, Y, Z), which may each be set or adjusted automatically or by a user in terms of their component characteristic or their component value ($x_1, x_2, \ldots x_m; y_1, y_2, \ldots y_n; z_1, z_2, \ldots z_o$), so that a number ($|K|=m*n*o$) of combinations K of component values ($x_1, x_2, \ldots x_m; y_1, y_2, \ldots y_n; z_1, z_2, \ldots z_o$) may be set or adjusted at the measuring standard automatically and/or by the user;

a Calibration Database or Pool (CDB), wherein the Calibration Database or Pool (CDB) comprises $|CDB|$ combinations or sets of component values, wherein |CDB| is smaller than |K|; and a control unit programmed for calibrating the bioimpedance measuring device by using the measuring standard and setting—some or all or maximally all or each of—the |CDB| combinations of component values from the Calibration Database or Pool (CDB) at the measuring standard, but not by setting or adjusting more than the |CDB| combinations.

The measuring standard which is part of the medical set according to the present disclosure can optionally be according to the present disclosure. In some embodiments, it is not.

The medical measuring standard according to the present disclosure for use during calibrating a bioimpedance measuring device comprises contacts for electrically connecting the measuring standard to measuring electrodes and to signal electrodes of the bioimpedance measuring device.

In some embodiments, the method described herein for testing a bioimpedance measuring device encompasses the steps:

providing a bioimpedance measuring device;

providing at least one measuring standard according to the present disclosure and setting the adjustable component values of the measuring standard to predetermined values;

connecting the bioimpedance measuring device with the electrodes of the measuring standard;

assuming or calculating component values of the measuring standard by the bioimpedance measuring device;

comparing the assumed or calculated component values with the set component values; and evaluating the result of the comparison. The evaluation may be a comparison with a pre-set threshold or the like.

The bioimpedance measuring devices according to the present disclosure may be calibrated by the method according to the present disclosure, it may be in signal communication with the medical set according to the present disclosure, it may comprise a measuring standard according to the present disclosure, and/or it may be tested by the method according to the present disclosure.

Advantageous developments of the present disclosure may be each subject matter of the dependent claims and embodiments.

Whenever an embodiment is mentioned herein, it is to be understood as an exemplary embodiment according to the present disclosure.

Embodiments according to the present disclosure may comprise one or several of the features mentioned herein in any feasible combination.

In some embodiments, the methods encompass providing a Patient Database (short: PDB) with |PDB| combinations or sets of information, (|PDB| being preferably a higher number than |CDB|), wherein each of these combinations comprises the following information:

a) optional: Patient parameters which may be used to characterize a patient or a specific patient, wherein the patient parameters are not bioimpedance measuring results; and b) a plurality of bioimpedance measuring results measured for the specific patient on at least one previous bioimpedance measuring over a frequency range or at a plurality of frequencies being different from each other.

In these embodiments, the method also encompasses determining or providing |CDB| combinations of component values of the measuring standard, based on which the bioimpedance measuring results of at least a predetermined part (e. g., a percentage, a predetermined section of the Gaussian normal distribution, a particular subset, or the like) of the |PDB| combinations of the Patient Database (PDB) may be gained using Cole Models or Cole-Cole Plots (this can be achieved, e. g., by using one or more predetermined mathematical methods).

In these embodiments, the method also encompasses establishing or creating the Calibration Database or Pool (CDB) from the thus determined |CDB| combinations of component values.

In certain embodiments, the method according to the present disclosure also encompasses filtering the Patient Database (PDB) according to predetermined criteria in order to create the Calibration Database or Pool (CDB) based on the Patient Database (PDB). Further, in order to create the Calibration Database or Pool (CDB), only the |CDB| combinations of component values thus filtered out of the Patient Database (PDB) are used.

In particular embodiments of the present disclosure the predetermined criteria relate to characteristics of patients to be treated, in particular their age, race, height, weight, gender, health state, particular diseases, and so on.

In some embodiments of the present disclosure, the step of calibrating the bioimpedance measuring device is carried out regularly (every week, for example) and/or repeatedly (several times a year, for example). The control unit may be programmed accordingly.

In certain embodiments of the present disclosure, the calibration results (e. g., a deviation between what has been determined by the bioimpedance measuring device and what should have been determined by that device based on the true component values of the measuring standard used) gained by performing the calibrating method at different points of time are compared to each other and deviations from each other are determined. The control unit may be programmed accordingly.

In some embodiments of the present disclosure, for carrying out the step of calibrating the bioimpedance measuring device using the measuring standard, measuring electrodes and signal electrodes of the bioimpedance measuring device are connected to contacts of the measuring standard.

In certain embodiments of the present disclosure, calibration is the comparison of measurement values delivered by a device under test conditions with those of a calibration standard of known accuracy. Such a standard could be another measuring device of known accuracy, a device generating the quantity to be measured.

In some embodiments of the present disclosure, the term "calibrating" can be replaced by the term "adjusting", and a calibration process may be an adjusting process, and so on. In those embodiments, both terms (or word families) are interchangeable with each other whenever used throughout the present application.

In certain embodiments of the present disclosure, the step of calibrating starts automatically when the measuring electrodes and the signal electrodes of the bioimpedance measuring device have been connected to contacts of the measuring standard. The control unit may be programmed accordingly.

In some embodiments of the present disclosure, the step of calibrating starts after a time condition. Also, the measuring electrodes and the signal electrodes of the bioimpedance measuring device have to be connected to contacts of the measuring standard.

Real components are not only subject to a value mismatch due to manufacturing, but may exhibit sensitivity to changes in temperature for example. In particular, resistors may have a distinct temperature dependency depending on their design. Accordingly, it may be provided that a temperature, e.g., the temperature of the components that is currently prevailing during the calibration process, which may in a good approximation be the temperature of the direct surroundings of the components during the calibration step, is included in determining the resulting impedance and is accordingly taken into account during the calibration process.

Therefore, in some embodiments the methods encompass determining a prevailing or surrounding temperature, preferably by a temperature sensor, to which temperature the bioimpedance measuring device and/or the measuring standard is exposed during the calibration. Also, the prevailing temperature of the surroundings during calibration is taken into account.

In certain embodiments, the calibrating step is performed by the manufacturer of the bioimpedance measuring device. Hence, the bioimpedance measuring device does not need to comprise a measuring standard of its own.

In some embodiments, the method encompasses establishing a signal communication between the measuring standard and at least one of the Calibration Database or Pool (CDB) and the Patient Database (PDB). Also, the Calibration Database or Pool (CDB) is read (directly or indirectly) by the measuring standard. The control unit may be programmed accordingly.

In certain embodiments, the method encompasses indicating how precise the result of the calibration is. For example, the medical set, or any other device according to the present disclosure, may comprise an indicator (monitor, printer, or the like) configured to indicate a quantitative and/or qualitative precision or reliability of the calibration status achieved. For example, the indicator may indicate precision based on how many combinations of component values of the measuring standard the calibration process was carried out on. Also, the size of the Calibration Database or Pool (CDB) or the Patient Database (PDB), or the numbers of their entries, may be indicated, e. g., in absolute or relative numbers.

In some embodiments, the method encompasses updating or automatically updating at least one of the Calibration Database or Pool (CDB) and the Patient Database (PDB). The control unit may be programmed accordingly.

In some embodiments, the sets described herein comprise:
a Patient Database (PDB) comprising or consisting of |PDB| combinations or sets of information, wherein each of these combinations comprises at least the following information:
  a) optional: Patient parameters which may be used to characterize a patient or a specific patient, wherein the patient parameters are not bioimpedance measuring results; and
  b) a plurality of bioimpedance measuring results measured for the specific patient on at least one previous bioimpedance measurement over a frequency range (or at a plurality of frequencies being different from each other).

In these embodiments, the control unit is programmed for determining or providing at least one of the |CDB| combinations of component values of the measuring standard, based on which the bioimpedance measuring results of at least a predetermined part of the |PDB| combinations of the Patient Database (PDB) may be gained using Cole Models or Cole-Cole Plots; and it is also programmed for establishing or creating the Calibration Database or Pool (CDB) from the thus determined |CDB| combinations of component values.

In some embodiments the control unit is programmed for filtering the Patient Database (PDB) according to predetermined criteria in order to create the Calibration Database or Pool (CDB) from the Patient Database (PDB), wherein in order to create the Calibration Database or Pool (CDB), only the |CDB| combinations of component values thus filtered out of the Patient Database (PDB) are used.

In certain embodiments the control unit is programmed for comparing the calibration results of the steps of calibrating, performed at different points of time, to each other and determining the deviations from each other.

In some embodiments, the control unit is programmed for automatically performing the step of calibrating when the measuring electrodes and the signal electrodes of the bioimpedance measuring devices have connected to contacts of the measuring standard In some embodiments, the control unit is programmed for performing the step of calibrating after a time condition, and also under the condition that the measuring electrodes and the signal electrodes of the bioimpedance measuring device have been connected to contacts of the measuring standard.

In certain embodiments, the set comprises a temperature sensor. In these embodiments the control unit is programmed for determining a prevailing or surrounding temperature, preferably by a temperature sensor, to which temperature the bioimpedance measuring device and/or the measuring standard are exposed during the calibration. The control unit is programmed for taking the prevailing or surrounding temperature into account during calibration.

In some embodiments, the control unit is programmed for establishing a signal communication between the measuring standard and at least one of the Calibration Database or Pool (CDB) and the Patient Database (PDB) and for reading the Calibration Database or Pool (CDB) (directly or indirectly) by the measuring standard.

In certain embodiments, the control unit is programmed for updating or automatically updating at least one of the Calibration Database or Pool (CDB) and the Patient Database (PDB).

In some embodiments, the set comprises a bioimpedance measuring device to be calibrated or already calibrated according to the present disclosure.

In certain embodiments, in the measuring standard a first parallel circuit of a first, preferably single, resistor (not being in series circuit with a capacitance) on the one hand and a first series circuit of a second resistor and a first capacitance on the other hand are arranged in parallel between two contacts of the measuring standard.

In some embodiments, in the measuring standard a second parallel circuit is arranged in parallel circuit to the first parallel circuit, the second parallel circuit being or comprising a second series circuit of a third resistor with a second capacitance.

In certain embodiments, in the measuring standard further parallel circuits each having a further series circuit of a further resistor and a further capacitance are each arranged parallel to the first parallel circuit.

In some embodiments, the bioimpedance measuring device is in signal communication with the control unit of the medical set. For example, the bioimpedance measuring device and the control unit of the medical set may be programmed to be able to communicate via a correspondingly configured interface, respectively.

In certain embodiments, the bioimpedance measuring device according to the present disclosure may be designed to measure as described, e. g., in U.S. Pat. Nos. 5,063,937, 4,291,708 and 4,539,640.

Some or all embodiments according to the present disclosure may comprise one, several or all of the aforementioned and/or the following stated advantages.

As is described in more detail below, calibrating a bioimpedance measuring device may be complicated and, above all, also time-consuming and thus expensive. In fact, the calibration procedure—which has to be done with each and every bioimpedance measuring device—takes some time (hours to days). As shown supra and further elaborated on infra, the calibration methods described herein facilitate a faster calibration process without neglecting accuracy and/or security aspects.

Another advantage of the invention may be seen in the collection of impedance values gained from bioimpedance measurements on real patients in a Patient Database from which information about component value combinations for the measuring standard can be deducted which matters in the reality of a clinic setting.

Embodiments of the present disclosure are explained using accompanying figures in which identical reference numerals refer to same or similar components.

DETAILED DESCRIPTION OF THE INVENTION

Figure 1:
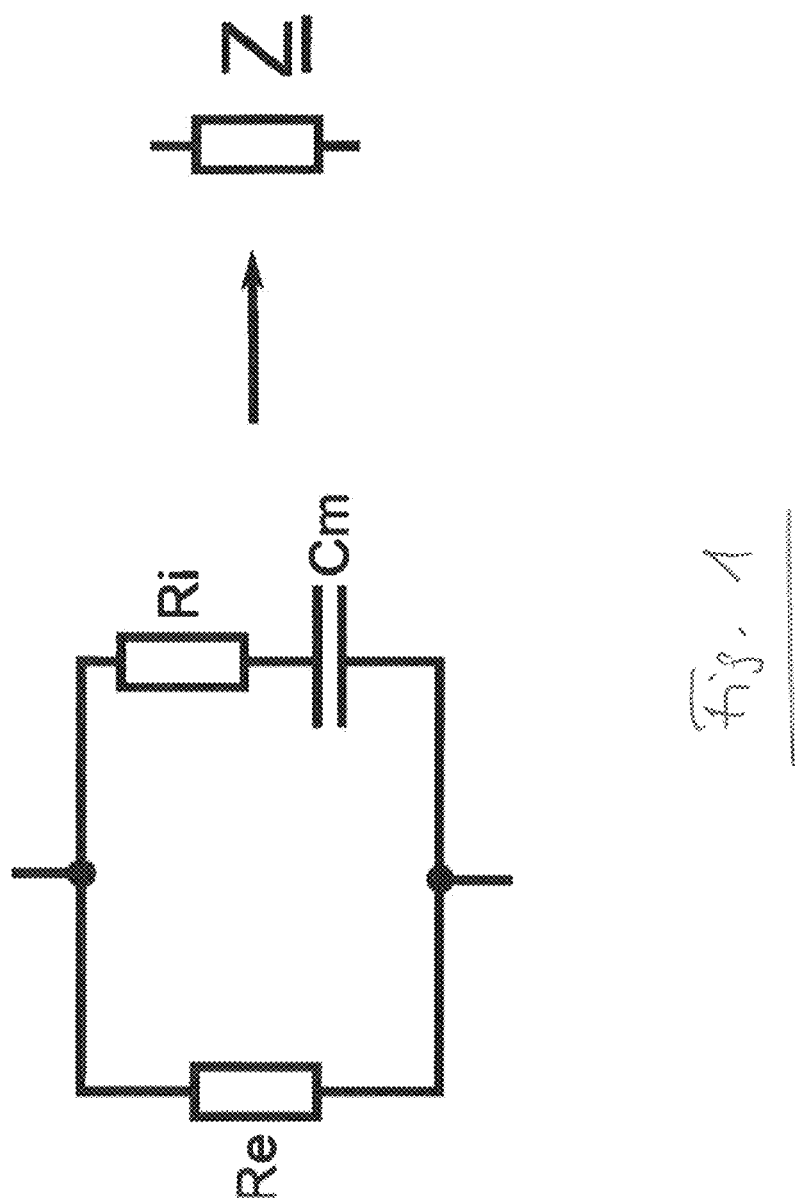
FIG. 1 shows schematically simplified a Cole Model as referred to in this specification.
Figure 2:
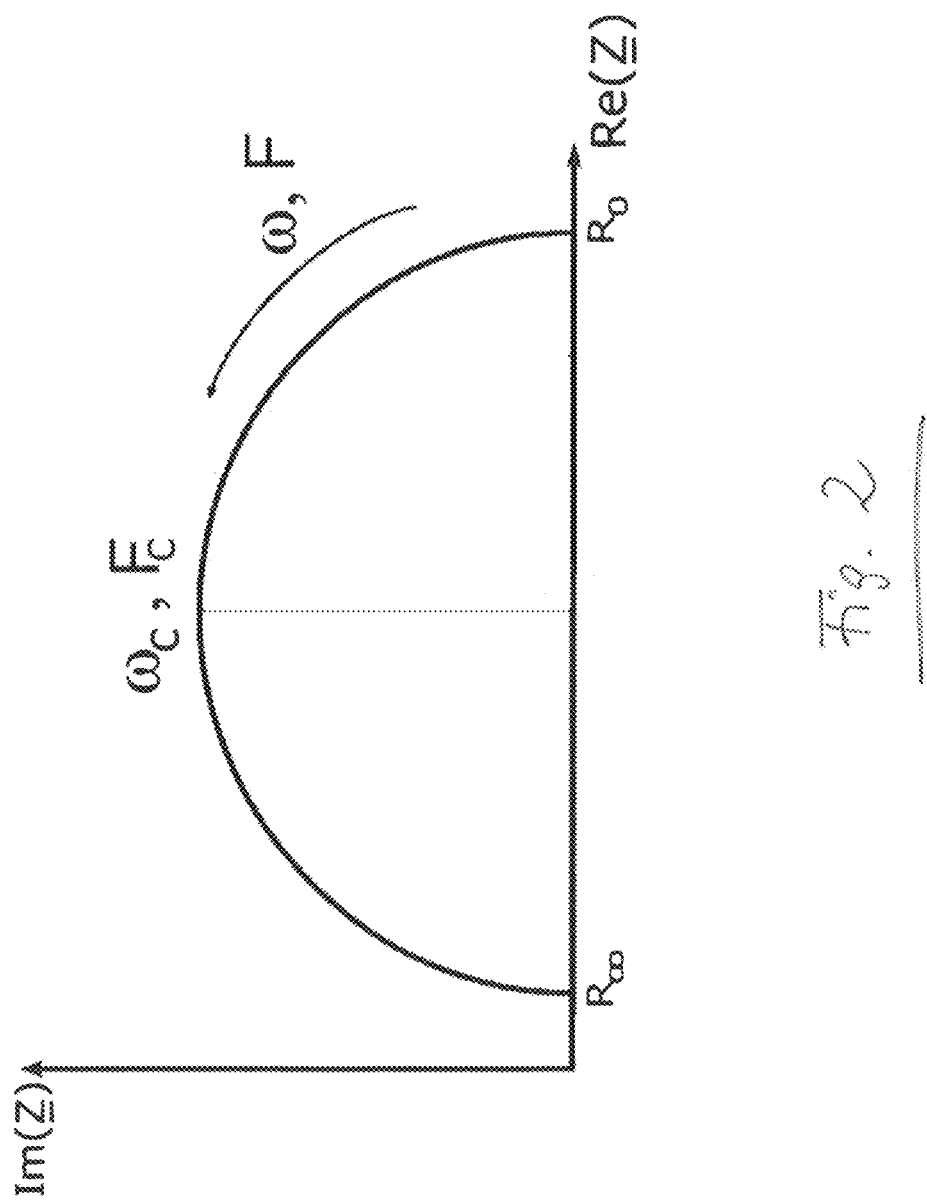
FIG. 2 shows a Cole Cole Plot as referred to in this specification.

FIG. 1 shows a common modeling of human tissue by electrical components, known as the Cole Model. This model provides a typical (idealized) impedance curve as shown in FIG. 2 when determining the impedance across all frequencies as outlined below. The resistors $R_0$ and $R\infty$ are purely resistive, i.e., there is no reactance (Im($\underline{Z}$)=0). The impedance with the largest reactance Im($\underline{Z}$) component can be observed at a typical frequency (characteristic frequency $\omega c$ or Fc).

Depending on the component values $x_1, x_2, \ldots x_m$; $y_1, y_2, \ldots y_n$; $z_1, z_2, \ldots z_o$ and the applied frequency $\omega$, the left-hand module results in a certain point on the a.m. impedance curve. For DC (frequency=0), the capacitance Cm is an interruption, hence the resulting value for the impedance is Z=Re. Thus, in the Cole Cole Plot of FIG. 2 $R_0$ corresponds to Re. At infinite frequency, the capacitance Cm behaves as a short circuit and hence the resulting value for the impedance becomes the parallel combination of Re and Ri shown in FIG. 1 leading to the Rinf in the Cole Cole plot of FIG. 2.

Each Cole Cole Plot corresponds to a characteristic assembly of the Cole Model with specific component values $x_1, x_2, \ldots x_m$; $y_1, y_2, \ldots y_n$; $z_1, z_2, \ldots z_o$. These are determined from the impedance measurement on the patient and these values are used to calculate patient parameters, such as overhydration, that are important for the prescription.

Bioimpedance measuring devices have to be calibrated. This may be done using measuring standards. Such a measuring standard provides for the components, respectively, known or previously precisely measured component values, which are variable. A measuring standard may, schematically simplified, look like as shown in FIG. 3.

Figure 3:
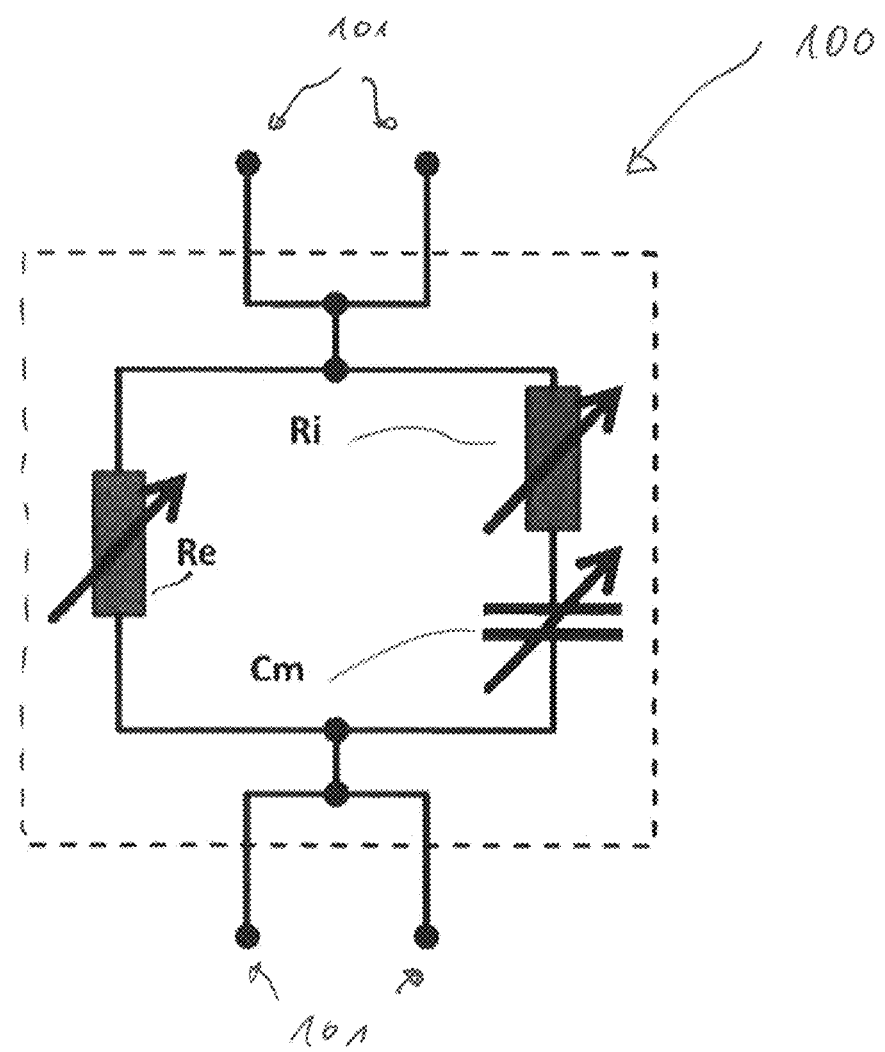
FIG. 3 shows a measuring standard used in the method according to the invention.

The measuring standard 100 shown in FIG. 3 may have variable components Re, Ri and Cm whose values can be adjusted by the user. Since adjusting the component values has an effect on the impedance to be measured by the bioimpedance measuring device, the measuring standard 100 may also be referred to as a Multi-impedance Box (short: MIB).

The measuring standard 100 essentially embodies the circuit of the Cole Model with selectable component values. There are several ways to design the measuring standard 100 accordingly. For example, components of the measuring standard 100 can be connected to each other via relays. However, the (e.g., electromechanical) relays can be replaced by semiconductor circuits (e. g., transistors, transmission gates, electronic switches). It is also possible that instead of selectable component combinations single specific components of high accuracy are used, the values of which are made known to the calibration system, whereby the set or adjusted impedance Z can be calculated.

The following typical values can be set for the component values in an exemplary embodiment of the measuring standard 100:

TABLE

| Measuring standard parameter range | |
|---|---|
| Re [Ohm] | 249.7 . . . 1207 (32 steps) |
| Ri [Ohm] | 714.9 . . . 3058.17 (32 steps) |
| Cm [nF] | 0.36 . . . 4.352 (16 steps) |

As can be seen from this table, the exemplary measuring standard 100 of FIG. 3 comprises only three components Re, Ri and Cm. These three components may herein be referred to in a more general manner as X, Y, Z. The component values shown in the table as selectable or adjustable for Re, Ri and Cm are, hence, referred to as component values $x_1, x_2, \ldots x_m$; $y_1, y_2, \ldots y_n$; $z_1, z_2, \ldots z_o$ with $x_1$ being 249.7, $x_m$ being 1207, $y_1$ being 714.9, $y_n$ being 3058.17, $z_1$ being 0.36 and $z_o$ being 4.352. In the present example, between $x_1$ and $x_m$ the user can select one of 32 steps (here: m=32), between $y_1$ and $y_n$ the user can select one of 32 steps (here: n=32) and between $z_1$ and $z_o$ he can select one of 16 steps (here: o=16). For example, the combination of $x_1$, $y_1$, and $z_1$ could be a first combination K1, the combination of $x_1$, $y_1$, and $z_2$ could be a second combination K2, and so on.

The components values of the table above are typical when assessing or measuring the impedance. In fact, these values may be used to characterize subject specific lumped parameter models that represent the largest possible part of, or even the entire, population.

Running the above-shown adjustable component values through their available value ranges will result in 16384 ("|K|") selectable component value combinations K (32*32*16=16384), each combination reflecting a different impedance according to the Cole Model. It is noted that since each of the |K| combinations results in a Cole Cole Plot itself as many different Cole Cole Plots may be drawn. Also, it goes without saying that if additional component values were selectably integrated into the measuring standard 100 or MIB, the number of resulting impedances would increase exponentially.

Figure 4:
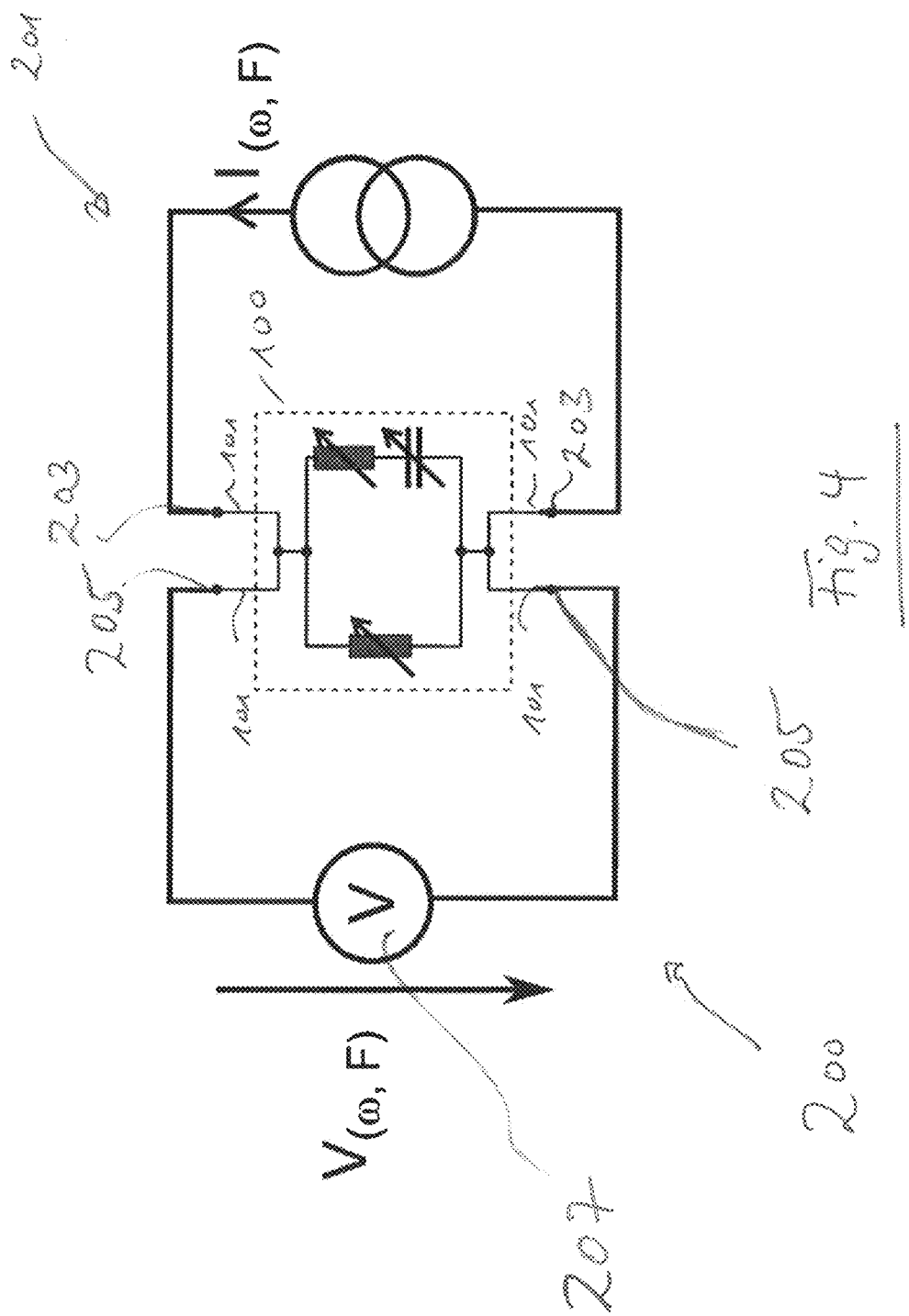
FIG. 4 shows how the bioimpedance measuring device may be calibrated using the measuring standard.

To fully calibrate the bioimpedance measuring device 200 in order to ensure high accuracy when measuring the bioimpedance of any patient, all of these combinations should be set with the measuring standard 100, and a Cole Cole Plot should be recorded for each combination. FIG. 4 shows how the bioimpedance measuring device 200 may be calibrated using the measuring standard 100.

FIG. 4 shows parts of a bioimpedance measuring device 200 comprising a signal generator 201 connected to a measuring standard 100 for the calibrating step.

In FIG. 4, the contacts 101 of the measuring standard 100 are in electrical contact with signal electrodes 203 and measuring electrodes 205, respectively.

The signal generator 201 of the bioimpedance device 200 to be calibrated applies the current I into the measuring standard 100 and varies the frequency of this test signal. The transducer 207 of the bioimpedance measuring device 200 simultaneously measures the voltage V across the measuring standard 100.

Since for contacting the measuring standard 100 the signal electrodes 203 and measuring electrodes 205 of the bioimpedance device 200 are advantageously used, they are also being calibrated.

From the phase shift and/or the ratio of or the relation between the amplitudes of I and V, and from the resulting phase shift between current and voltage, an impedance Z is calculated for the currently set frequency for $\omega$. The same procedure is repeated for as many different frequencies needed to be able to determine a Cole Cole Plot characteristic of the selected component values set at the measuring standard 100 for the calibration. The bioimpedance device 200 is programmed to calculate assumed component values based on these impedance values.

In a next step, the assumed component values are compared with the actual and set component values of the measuring standard 100. Deviations between the assumed component values and the actual and set component values may be used for generating correction data that in turn can be used to calibrate the bioimpedance measuring device 200. For example, such correction data can be stored in a nonvolatile memory of the bioimpedance measuring device. Alternatively, or additionally, correction data can also be kept available via a data connection with the bioimpedance measuring device using a unique device identification feature outside the device itself and retrieved as needed.

Alternatively, variable and/or adjustable components (such as potentiometers, variable capacitances) can also be provided inside the bioimpedance measuring device 200. Their corresponding values may be modified such that there is no longer any difference between component values calculated by the bioimpedance measuring device 200 and the real and actually set component values of the components comprised by the measuring standard 100.

It can be seen from this that the calibration process is complicated, time-consuming and expensive.

However, reducing the number of component value combinations of the measuring standard 100 without waiving safety aspects is possible and suggested by the present disclosure. For example, calibration of a bioimpedance measuring device 200 based on only a limited number of possible component value combinations has been found possible and also reliably by the inventors if, e. g., particularities of patients belonging to a particular population group are observed. For example, this can be achieved by using data from laboratory bioimpedance measurements of a large group of patients, and by classifying the patients in a Patient Databank (PDB) according to suitable criteria, e.g., their weight, gender, race, health state, diseases, and the like.

For example, the Patient Database PDB mentioned herein may comprise patient parameters which may be used to characterize a specific patient (e.g., weight, gender, race, and the like), and also bioimpedance measuring results measured for the specific patient on at least one previous bioimpedance measuring over a frequency range.

Hence, having a particular patient in mind, one might segregate the theoretically possible combinations of component values of the measuring standard 100 into those which will not be of relevance for the particular patient and which do not have to be considered in the calibration process and those which will be of essence and which will have to be considered when calibrating the bioimpedance measuring device 200.

Thus, assessing a Patient Database PDB before calibrating the bioimpedance measuring device 200 as set forth herein makes it possible to classify a variety of combinations of component values of the measuring standard 100 as irrelevant for the following calibration step. Consequently, such combinations do not need to be measured and calibration data need not be created using those combinations. This segregation may significantly shorten the calibration process for a bioimpedance measuring device 200 without the risk of performing uncalibrated measurements later on on real patients.

Obviously, the more entries the PDB has, the more precisely relevant values of bioimpedance measurements can be extracted from the PDB.

Real capacitances are themselves complex impedances, i.e. they include series and/or parallel resistors and inductances, resulting in a frequency-dependent impedance. Hence, in some embodiments, it is provided that this characteristic is also taken into account in the capacitance Cm of the measuring standard 100. Hence, the component values of those components or "sub-components" (their values also being called "sub-component values" here) could in some embodiments made be part of the combinations of component values. It is noted that identifying them (or their size) might be used as further hints towards the real impedance of the patient and/or towards more precise findings regarding the patient if they are acknowledged in the assessment of the patient's condition.

The calibration can be done anytime and repeatedly. Thus, in some embodiments, the bioimpedance measuring device 200 comprises its own measuring standard 100 and may have access to the Patient Database PDB. This access can be advantageously based, e.g., on a secure data connection (e.g., network) to a central entity (e. g., server), for example via any wireless interface, e.g., Wi-Fi peer-to-peer, Bluetooth or infrared interfaces. Using USB sticks or other data carriers is also conceivable and comprised by the present disclosure.

One advantage of such a solution may be that the Patient Database PDB can be constantly updated based on ongoing laboratory measurements of future patients and it may be available during calibration in its most recently updated version. Thus, if there is, for example, an unexpected laboratory measurement of a specific patient, which makes a calibration step based on further combination of component values of the measuring standard 100 necessary, then this can be conveniently initiated "online", without having to send the bioimpedance measuring device 200 back to the manufacturer for an update.

The measuring standard 100 may be an integral part of the bioimpedance measuring device 200, or may be designed as a stand-alone device that is used for a plurality of bioimpedance measuring devices 200.

It can be envisaged that the bioimpedance measuring device 200 is recalibrated regularly. For this purpose, in particular if the measuring standard 100 and the control unit needed for carrying out the calibration method are an integral part of the bioimpedance measuring device 200, a corresponding message may be output via an output device of the bioimpedance measuring device 200 requesting the user to contact the signal electrodes 203 and the measuring electrodes 205 to each other or to contacts 201 of the measuring standard 100 analogously to FIG. 4. The calibration process is started thereafter.

This provision may be used, for example, to detect defective or overaged components, when the comparison of the results of the current calibration process with results of a previous calibration shows abnormalities. For example, a deviation of the results from the true (or set) component values may exceed a threshold that had not been exceeded during earlier calibration steps. Also, a deviation may be discovered when comparing the present deviation from the true component values with earlier deviations from the true component values.

In some embodiments it can be provided that every time selected electrical contacts provided on the bioimpedance measuring device 200 (e. g., the signal electrodes 203 and/or the measuring electrodes 205) are connected to electrodes 101 of the measuring device 100 (e. g., analogously to what is shown in FIG. 4) the calibration step starts automatically.

In some embodiments, it can be provided that a calibration according to the present disclosure takes place automatically when both the electrodes provided for the calibration process are connected to their corresponding contacts and a time condition is met. For example, the control unit triggering the automatic start of the calibration step may be programmed to start the calibration at a predetermined, settable time of the day (e.g. at night). This embodiment may allow the bioimpedance measuring device 200 to be calibrated at night, or on the weekends, or at any other suitable time when the calibration process does not hamper the use of the device 200. Yet, this way the bioimpedance measuring device 200 may always be found by the user in a perfectly and recently calibrated condition.

In some embodiments, the calibration process may be performed prior to using the bioimpedance measuring device 200 for measuring the bioimpedance of a specific patient. In this case, the calibration process can advantageously be further accelerated if the number of combinations of component values of the measuring standard 100 is further reduced by certain characteristics of the patient (e.g. race, age, height, weight, gender).

Consequently, in some embodiments the Patient Database PDB is indexed to these criteria and can be filtered accordingly. Thus, a kind of "quick test" of the calibration status based on the most relevant component value combinations can be done before using the bioimpedance measuring device for measuring a patient's impedance by calibrating the device only based on some combinations of component values (namely the ones extracted from the Patient Database PDB in the light of the criteria input). It might be provided that if there are relevant differences when compared to a previous "complete calibration", this then may indicate a problem which may be shown or displayed and corresponding actions (using another bioimpedance measuring device, for example) can be taken. Again, this may increase patient safety.

Figure 5:
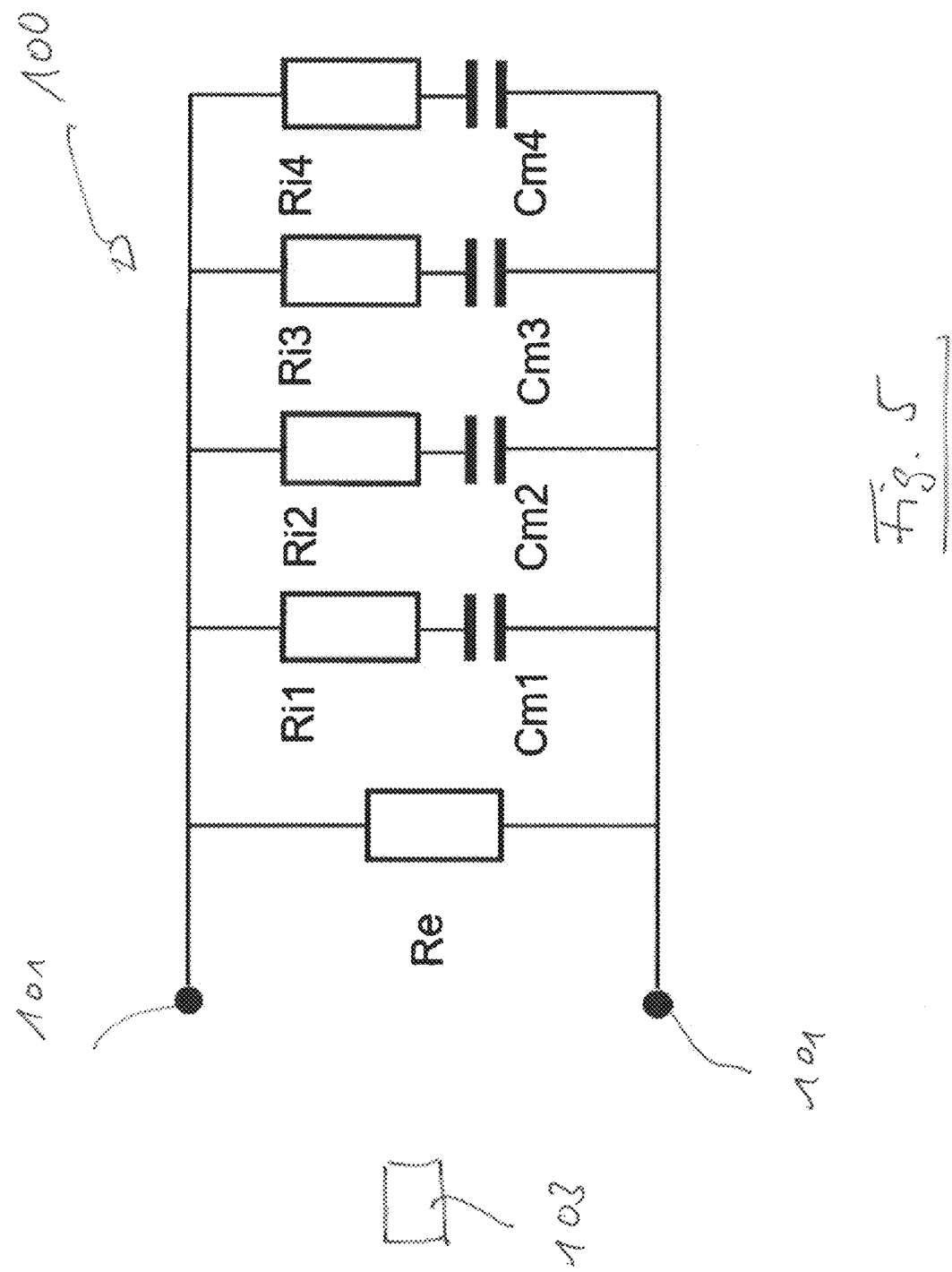
FIG. 5 shows a medical measuring standard according to the invention.

FIG. 5 shows the basic design of a measuring standard 100 according to an exemplary embodiment of the present disclosure.

The measuring standard 100 according to the present disclosure comprises not only a series circuit of the second resistor Ri1 with the first capacitance Cm1 as already known from FIG. 3 or FIG. 4 but also at least one further series circuit of a third resistor Ri2 with a second capacitance Cm2. The combination of Ri2 and Cm2 is parallel connected to the second resistor Ri1 and the first capacitance Cm1.

Also, as shown in FIG. 5, the measuring standard 100 may comprise further parallel circuits each having or consisting of a series circuit of yet another resistor with yet another capacitance Ri3, Cm3 or Ri4, Cm4, and so on.

Preferably, the measuring standard 100 comprises two (Ri2, Cm2, Ri3, Cm3) and particularly preferably three further parallel connected series circuits of a resistor with a capacitance (Ri2, Cm2, Ri3, Cm3, Ri4, Cm4) each.

Exemplary component values of the components shown in FIG. 5 that may be characteristic for a particular patient, can be as follows:

Re=511 Ohm; Ri1=5110 Ohm; Ri2=28700 Ohm; Ri3=3010 Ohm; Ri4=3010 Ohm; Cm1=0.1 nF; Cm2=1.5 nF; Cm3=0.47 nF; Cm4=2.2 nF

This combination of component values thus simulates a specific patient by a model called the extended impedance model herein. This extended impedance model is reflected by the design shown in FIG. 5. Other values may be specific for other patients. The values selected for the components are determined experimentally. For this purpose, a patient may be measured with a calibrated bioimpedance measuring device 200 and an impedance curve may be recorded.

Subsequently, the component values of the extended impedance model may be determined using mathematical methods, which result in the most exact possible match with the measure of values (curve fitting, least square, and the like).

As has been stated above, the Cole Model discussed with regard to FIG. 1 is used in practice in order to simulate the impedance of the human body, and findings regarding the human body (overhydration, hydration status, fluid volume, lean tissue, fat tissue, and so on) are derived from the Cole Model and from Cole Cole Plots drawn based on the Cole Model.

It has been observed that impedance curves resulting from the extended impedance model shown in FIG. 5 match better with the real measurements on patients than curves gained from the basic Cole Model shown in FIG. 1 and discussed with respect to FIG. 3 and FIG. 4.

Figure 6:
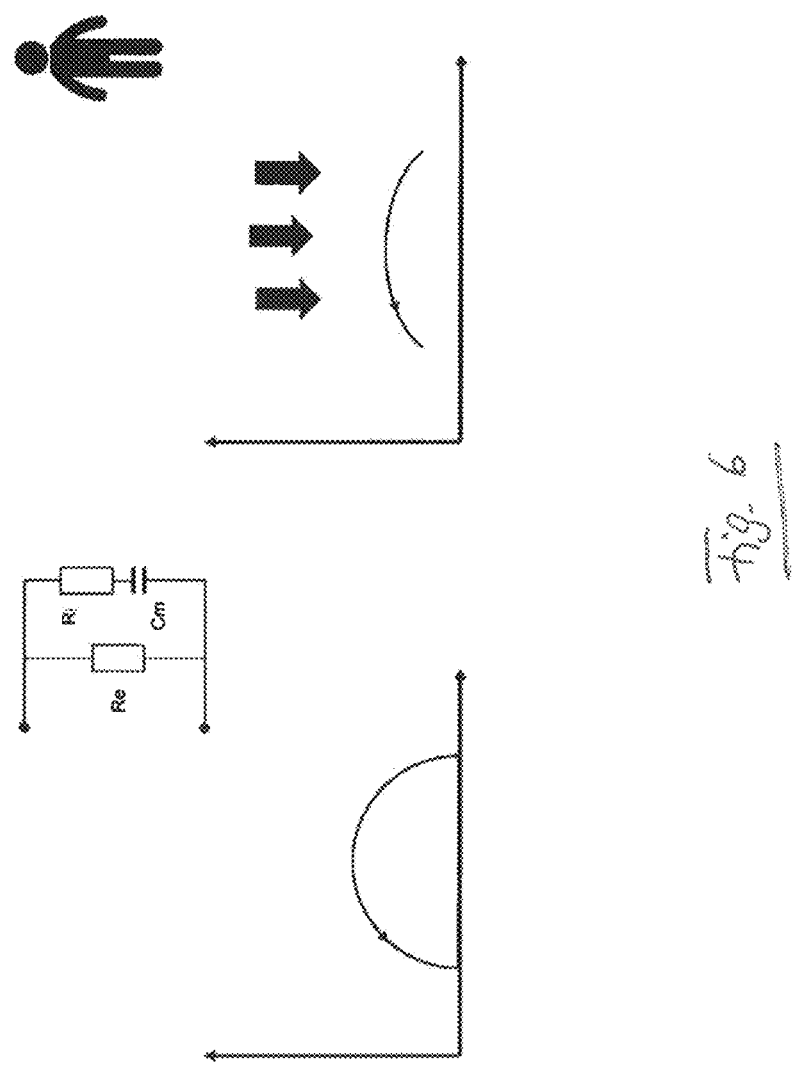
FIG. 6 compares impedance curves gained when using a 3-component Cole Model and when measuring a patient.

The divergence between the results gained from the Cole Model of FIG. 1 and the practice is indicated in FIG. 6.

An optional temperature sensor 103 may be provided.

Figure 7:
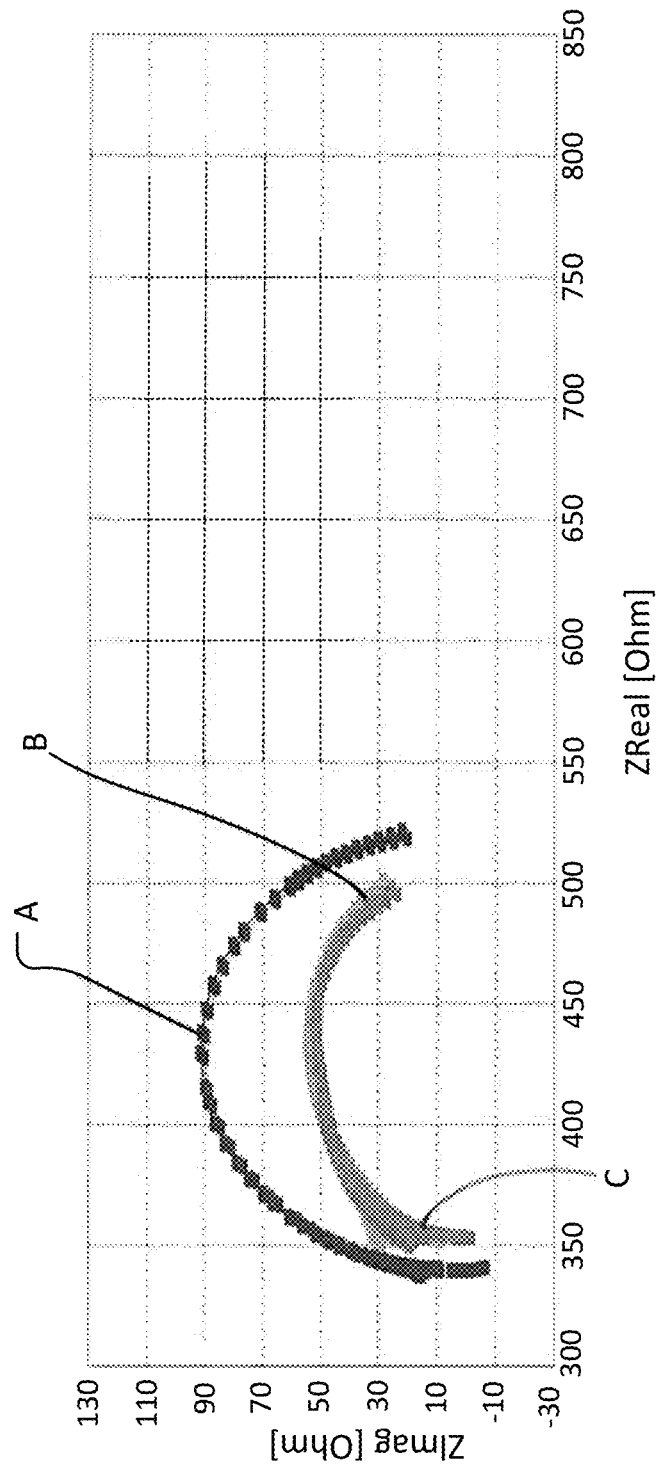
FIG. 7 shows a comparison between a curve A of impedance values gained from the Cole Model shown in FIG. 1, a curve B gained from the extended impedance model discussed with respect to FIG. 5 and a curve C gained directly from a real or living, respectively, patient.

FIG. 6 shows that while using the known 3-component Cole Model results in a perfect semicircle in the impedance plane (left), the reality (values measured on a patient) is reflected in a compressed circular arc (right). The effect of the compressed circular arc is represented by the extended impedance model according to the present disclosure as exemplarily shown in FIG. 5. FIG. 7 shows the difference.

FIG. 7 shows a comparison between a curve A of impedance values gained from the known Cole Model shown in FIG. 1, a curve B gained from the extended impedance model shown in FIG. 5 and a curve C gained directly from a real patient.

As can be seen from FIG. 7, the results gained from the extended impedance model shown in FIG. 5 (curve B) are much closer to the real values derived from the patient in question (curve C).

Hence, the use of the extended impedance model shown in FIG. 5 results in a much better match with reality.

The extended impedance model makes it possible to test bioimpedance measuring devices 200 under more realistic conditions without the need to measure real patients. In contrast to measurements on patients, the measurement with the extended impedance model shown in FIG. 5 is reproducible and accurate at all times.

Thus, the extended impedance model is well suited for quality control of bioimpedance measuring devices 200.

Figure 8:
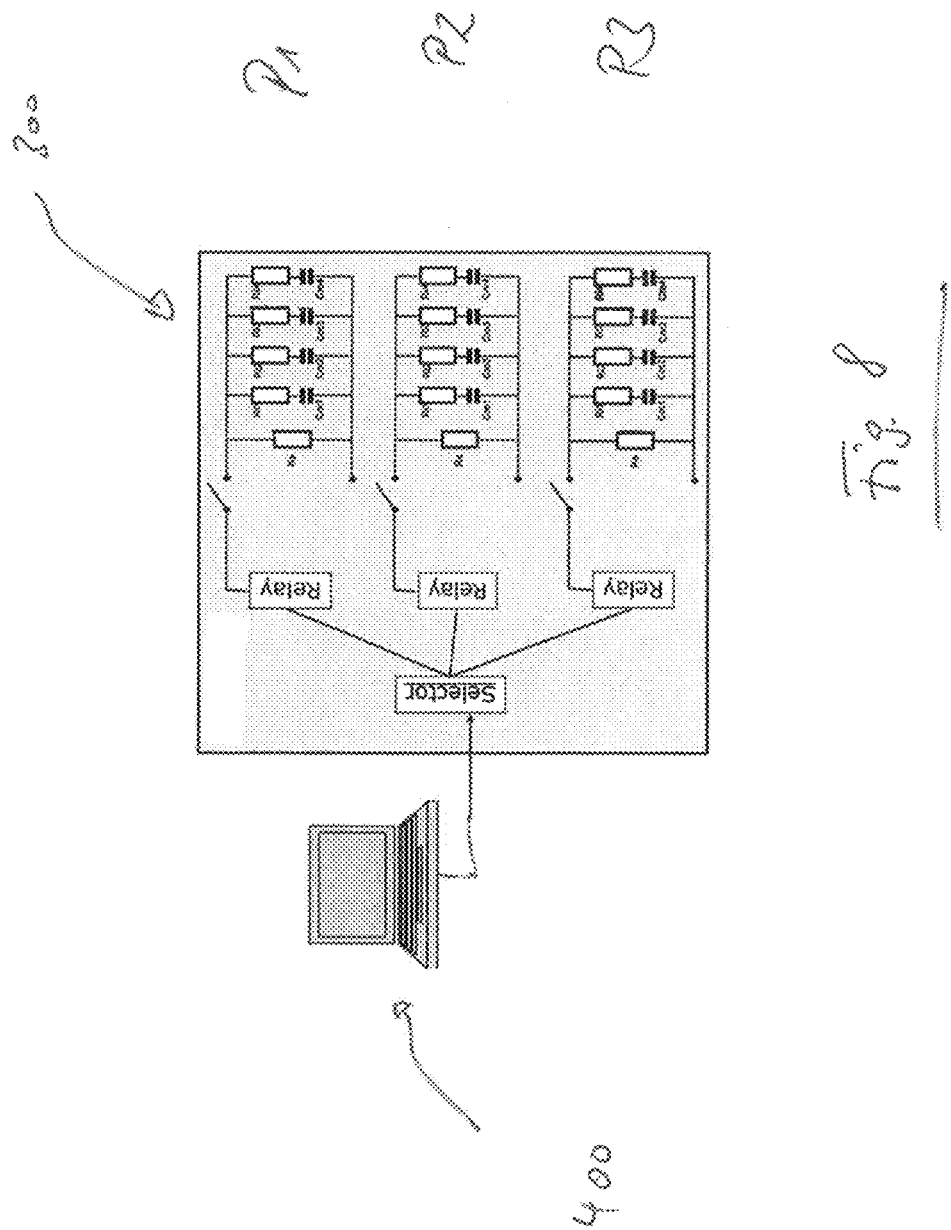
FIG. 8 shows a test box for testing a bioimpedance measuring device using differently configured implementations of the extended impedance model discussed with respect to FIG. 5.

FIG. 8 shows that differently configured implementations of the extended impedance model according to the present disclosure (see, e.g., FIG. 5) can be selected in a test box 300.

The test box 300 may comprise more than one measuring standard 100 (here: three) whose adjustable component values (Re, Ri1, Ri2, Cm1, Cm2, . . . ) are set to different predetermined values.

A bioimpedance measuring device 200 to be tested is connected to the test box 300 (as in FIG. 4), the controlling computer 400 successively selects the implementation simulating a specific real patient (e.g., Patients P1, P2, P3), and the bioimpedance measuring device 200 records an impedance curve for each of the simulated Patients P1, P2 and P3, respectively.

The thus gained impedance curve is compared (by the computer 400, for example) with the reference curve resulting from the respective connection, whereby statements about the measurement accuracy and thus realistic quality control are possible.

In some embodiments, the extended impedance model is used in the same way as described above for the calibration of the bioimpedance measuring device 200 using the known Cole Model.

Figure 9:
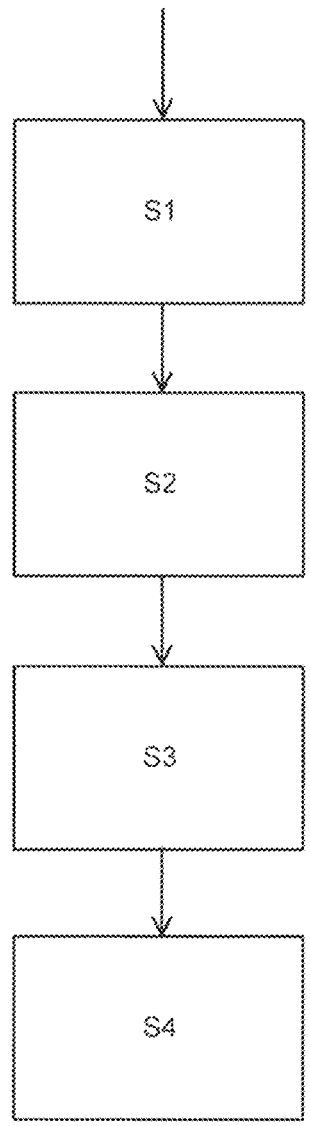
FIG. 9 shows in a simplified manner an embodiment of the method for calibrating a bioimpedance measuring device according to the invention.

FIG. 9 shows in a simplified manner an embodiment of the method for calibrating a bioimpedance measuring device according to the invention.

The method encompasses in a first step S1 providing a bioimpedance measuring device 200.

In another step S2 it encompasses providing a measuring standard with a plurality of components (X, Y, Z), which may each be set or adjusted automatically and/or by a user in terms of their component characteristic or their component value $(x_1, x_2, \ldots x_m; y_1, y_2, \ldots y_n; z_1, z_2, \ldots z_o)$, so that a number ($|K|=m*n*o$) of combinations K of component values may be set or adjusted at the measuring standard automatically and/or by the user.

The method also encompasses in a step S3 providing a Calibration Database or Pool (CDB), wherein the Calibration Database or Pool (CDB) comprises |CDB| combinations or sets of components values, wherein |CDB| is smaller than |K|.

The method also encompasses further in a step S4 calibrating the bioimpedance measuring device by using the measuring standard and setting some or each of the |CDB| combinations of component values from the Calibration Database or Pool (CDB) at the measuring standard, but not by setting or adjusting more than the |CDB| combinations.

Figure 10:
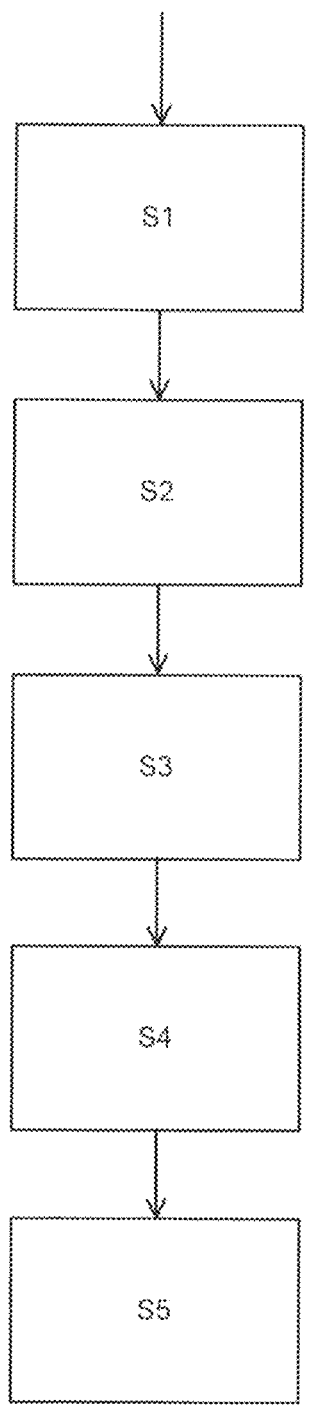
FIG. 10 shows in a simplified manner an embodiment of the method for testing a bioimpedance measuring device according to the invention.

FIG. 10 shows in a simplified manner an embodiment of the method according to the invention for testing a bioimpedance measuring device.

The method encompasses in a step S1 providing a bioimpedance measuring device 200.

The method encompasses in a step S2 providing at least one medical measuring standard and setting the adjustable component values of the measuring standard to predetermined values.

The method encompasses in a step S3 connecting the bioimpedance measuring device with the electrodes of the measuring standard.

The method encompasses in a step S4 assuming or determining component values of the medical measuring standard by the bioimpedance measuring device.

The method encompasses in a step S5 comparing the assumed component values with the set component values and evaluating the result of the comparison.

It is noted that the medical measuring standard according to the present disclosure discussed supra and exemplarily shown in FIG. 5 is a 5-path arrangement (having 5 parallel current paths) by way of example and merely illustrative. Indeed, fewer than or more than five paths may also be considered for the medical measuring standard suggested by the present disclosure.

Also, some or all of the several parallel paths may be identical to each other (i. e., comprise same components or be a repetition of the same structure or combination) or different from each other (i.e., comprise at least one component that is not comprised by each of the parallel paths, or be different structures of combinations).

LIST OF REFERENCE NUMERALS 100 (medical) measuring standard
101 contacts
103 temperature sensor
X, Y, Z components
$x_1, x_2, \ldots x_m$; component values of component X
$y_1, y_2, \ldots y_n$; component values of component Y
$z_1, z_2, \ldots z_o$ component values of component Z
A curve
B curve
C curve
CDB Calibration Database or Pool
|CDB| number of combinations comprised in the CDB
PDB Patient Database
|PDB| number of combinations comprised in the PDB
P1, P2, P3 patient
200 bioimpedance measuring device
201 signal generator
203 signal electrodes
205 measuring electrodes
207 transducer 300 test box
400 controlling computer

The invention claimed is:

1. A method for calibrating a bioimpedance measuring device, the method comprising the steps:
providing the bioimpedance measuring device;
providing a measuring standard with a plurality of components (X, Y, Z), that may each be adjusted in terms of their respective component value (x1, x2, ... xm; yi, y2, ... y; zi, z, ... zo), so that a number |K| of combinations of component values may be set, wherein |K|=m*n*o;
providing a Patient Database with a number |PDB| combinations of information, wherein each of the combinations of information comprises:
a) one or more patient parameters that characterize a specific patient, wherein the one or more patient parameters are not bioimpedance measurement results; and
b) a plurality of bioimpedance measurement results of the specific patient from at least one previous bioimpedance measurement process of the specific patient measured over a frequency range;
determining a number |CDB| of the combinations of component values based on which the plurality of bioimpedance measurement results of at least a predetermined part of the number |PDB| of combinations of the information may be gained using Cole Models or Cole-Cole Plots, wherein the number |CDB| is less than the number |K|;
providing a Calibration Database or Pool comprising the determined number |CDB| of the combinations of component values; and
calibrating the bioimpedance measuring device by using the measuring standard and adjusting the plurality of components (X, Y, Z) to some or all of the number |CDB| of the combinations of component values from the Calibration Database or Pool, but not by adjusting the plurality of components (X, Y, Z) to more than the number |CDB| of the combinations of component values.

2. The method according to claim 1, further comprising: filtering the Patient Database according to predetermined criteria in order to create the Calibration Database or Pool based on the Patient Database, wherein in order to create the Calibration, Database or Pool, only the number |CDB| of the combinations of component values thus filtered out of the Patient Database are used.

3. The method according to claim 2, wherein the predetermined criteria includes patient age, race, height, weight, or gender.

4. The method according to claim 1, wherein the calibrating the bioimpedance measuring device is carried out repeatedly at different points of time.

5. The method according to claim 4, wherein calibration results determined when carrying out the steps of calibrating performed at the different points of time, respectively, are compared to each other and deviations from each other are determined.

6. The method according to claim 1, wherein the calibrating the bioimpedance measuring device comprises connecting measuring electrodes and signal electrodes of the bioimpedance measuring device to contacts of the measuring standard.

7. The method according to claim 6, wherein the calibrating the bioimpedance measuring device starts automatically when the measuring electrodes and the signal electrodes of the bioimpedance measuring devices have been connected to the contacts of the measuring standard.

8. The method according to claim 6, wherein the calibrating the bioimpedance measuring device starts after the measuring electrodes and the signal electrodes of the bioimpedance measuring device have been connected to the contacts of the measuring standard and a time condition is met.

9. The method according to any claim 1, further comprising:
determining a prevailing temperature by a temperature sensor to which at least one of the bioimpedance measuring device and the measuring standard is exposed during the calibration; and
taking into account the determined prevailing temperature during the calibrating the bioimpedance measuring device.

10. The method according to claim 1, wherein the calibrating the bioimpedance measuring device is performed by a manufacturer of the bioimpedance measuring device.

11. The method according to claim 1, further comprising:
establishing a signal communication between the measuring standard and at least one of the Calibration Database or Pool and the Patient Database; and
reading the Calibration Database or Pool by the measuring standard.

12. The method according to claim 1, further comprising:
updating, or automatically updating, at least one of the Calibration Database or Pool and the Patient Database.

13. A medical set, comprising:
a bioimpedance measuring device;
a measuring standard with a plurality of components (X, Y, Z) that may each be adjusted in terms of their respective component value (x1, x2, ... xm; y1, y2, ... yn; z1, z2, ... zo), so that a number |k| of combinations of component values may be set, wherein |k|=m*n*o;
a Calibration Database or Pool comprising a number |CDB| of the combinations of component values, wherein the number |CDB| is smaller than the number |K|;
a control unit programmed for calibrating the bioimpedance measuring device by using the measuring standard and setting the plurality of components (X, Y, Z) to some or all of the number |CDB| of the combinations of component values from the Calibration Database or Pool, but not by setting more than the number |CDB| combinations of component values; and
a Patient Database having a number |PDB| combinations of information, wherein each of the combinations of information comprises:
a) one or more patient parameters that characterize a specific patient, wherein the one or more patient parameters are not bioimpedance measuring results; and
b) a plurality of bioimpedance measurement results of the specific patient from at least one previous bioimpedance measurement process of the specific patient measured over a frequency range;
wherein the control unit is programmed for: determining the number |CDB| of the combinations of component values based on which the bioimpedance measuring results of at least a predetermined part of the number |PDB| combinations of information may be gained using Cole Models or Cole-Cole Plots; and establishing or creating the Calibration Database or Pool comprises the determined number CDB| of the combinations of component values.

14. The medical set according to claim 13, wherein the control unit is programmed for: filtering the Patient Database according to predetermined criteria in order to create the Calibration Database or Pool from the Patient Database, wherein in order to create the Calibration Database or Pool, only the number |CDB| of the combinations of component values thus filtered out of the Patient Database are used.

15. The medical set according to claim 14, wherein the predetermined criteria includes patient age, race, height, weight, or gender.

16. The medical set according to claim 13, wherein the control unit is programmed for comparing calibration results determined when performing the calibrating at different points of time, respectively, to each other and determining deviations from each other.

17. The medical set according to claim 13, wherein the control unit is programmed for automatically performing the calibrating when measuring electrodes and signal electrodes of the bioimpedance measuring devices have been connected to contacts of the measuring standard.

18. The medical set according to claim 13, wherein the control unit is programmed for performing the calibrating after measuring electrodes and signal electrodes of the bioimpedance measuring device have been connected to contacts of the measuring standard and a time condition is met.

19. The medical set according to claim 13, further comprising a temperature sensor, and wherein the control unit is programmed for:
   determining a prevailing temperature by a temperature sensor to which temperature the bioimpedance measuring device and/or the measuring standard is exposed during the calibration; and
   taking into account the determined prevailing temperature during calibration.

20. The medical set according to claim 13, wherein the control unit is programmed for:
   establishing a signal communication between the measuring standard and at least one of the Calibration Database or Pool and the Patient Database; and
   reading the Calibration Database or Pool by the measuring standard.

21. The medical set according to claim 13, wherein the control unit is programmed for updating or automatically updating at least one of the Calibration Database or Pool and the Patient Database.

22. The medical set according to claim 13, further comprising a bioimpedance measuring device comprising measuring electrodes and signal electrodes, wherein the bioimpedance measuring device is in signal communication with the medical set.

23. A bioimpedance measuring device comprising measuring electrodes and signal electrodes, wherein the bioimpedance measuring device is calibrated by the method according to claim 1.

* * * * *

UNITED STATES PATENT AND TRADEMARK OFFICE
CERTIFICATE OF CORRECTION

PATENT NO. : 11,701,022 B2
APPLICATION NO. : 16/734921
DATED : July 18, 2023
INVENTOR(S) : Ulrich Moissl et al.

It is certified that error appears in the above-identified patent and that said Letters Patent is hereby corrected as shown below:

On the Title Page

Column 1 (Item (72) Inventors), Line 4, delete "Hosbach" and insert --Rosbach--.

Column 2 (Item (56) Other Publications), Line 1, delete "Impendance" and insert --Impedance--.

Column 2 (Item (56) Other Publications), Line 2, delete "Bio-Impendance" and insert --Bio-Impedance--.

Column 2 (Item (56) Other Publications), Line 7, delete ""Reconfigurabie" and insert --"Reconfigureable--.

Column 2 (Item (56) Other Publications), Line 7, delete "Bioimpendance" and insert --Bioimpedance--.

Column 2 (Item (56) Other Publications), Line 8, delete "Impendance" and insert --Impedance--.

In the Claims

Claim 1, Column 15, Line 8, delete "(X, Y, Z)," and insert --(X, Y, Z)--.

Claim 1, Column 15, Lines 9-10, delete "(x1, x2, . . . xm; yi, y2, . . . y; zi, z, . . . zo)," and insert --($x_1, x_2, \ldots x_m; y_1, y_2, \ldots y_n; z_1, z_2, \ldots z_o$),--.

Claim 1, Column 15, Line 13, after "|PDB|" insert --of--.

Claim 1, Column 15, Line 28, before "information" delete "the".

Claim 2, Column 15, Line 46, delete "Calibration," and insert --Calibration--.

Signed and Sealed this
Fifth Day of September, 2023

Katherine Kelly Vidal
*Director of the United States Patent and Trademark Office*

CERTIFICATE OF CORRECTION (continued)
U.S. Pat. No. 11,701,022 B2

Claim 13, Column 16, Lines 36-37, delete "(x1, x2, . . . xm; y1, y2, . . . yn; z1, z2, . . . zo)," and insert --($x_1, x_2, \ldots x_m; y_1, y_2, \ldots y_n; z_1, z_2, \ldots z_o$),--.

Claim 13, Column 16, Line 37, delete "|k|" and insert --|K|--.

Claim 13, Column 16, Line 39, delete "|k|" and insert --|K|--.

Claim 13, Column 16, Line 49, after "|CDB|" insert --of the--.

Claim 13, Column 16, Line 51, after "|PDB|" insert --of--.

Claim 13, Column 16, Line 66, after "|PDB|" insert --of--.

Claim 13, Column 17, Line 2, delete "comprises" and insert --comprising--.

Claim 13, Column 17, Line 2, delete "CBD|" and insert --|CDB|--.